United States Patent [19]

Iversen et al.

[11] Patent Number: 4,972,845
[45] Date of Patent: Nov. 27, 1990

[54] STOMA MEASURING DEVICE

[75] Inventors: Kent Iversen, Columbus; Ronald Isaac, Worthington, both of Ohio

[73] Assignee: Abbott Laboratories, Abbott Park, Ill.

[21] Appl. No.: 293,860

[22] Filed: Jan. 5, 1989

[51] Int. Cl.$^5$ ............................................. A61B 5/103
[52] U.S. Cl. ..................................... 128/780; 128/774
[58] Field of Search ................ 128/774, 780; 604/100, 604/119, 174, 175; 600/31, 32

[56] References Cited

U.S. PATENT DOCUMENTS

| | | | |
|---|---|---|---|
| 4,077,412 | 3/1978 | Moosun | 604/174 |
| 4,133,303 | 1/1979 | Patel | 128/774 |
| 4,356,824 | 11/1982 | Vazquez | 604/119 |
| 4,367,740 | 1/1983 | Evanoski, III | 604/100 |
| 4,534,542 | 8/1985 | Russo | 604/119 |
| 4,612,939 | 9/1986 | Robertson | 128/774 |
| 4,776,347 | 10/1988 | Matthews | 128/774 |
| 4,809,710 | 3/1989 | Williamson | 128/780 |
| 4,834,712 | 5/1989 | Quinn et al. | 604/175 |

Primary Examiner—Randall L. Green
Assistant Examiner—Karin Reichle
Attorney, Agent, or Firm—D. O. Nickey; E. H. Gorman; Patrick Phillips

[57] ABSTRACT

A stoma measuring device is provided comprising a valve housing containing a valve, a lumen with a port located near its distal end, with the lumen having its proximal end secured to the valve housing, and an inflatable component member, with this member located near the distal end of the lumen, the member having a first end secured to the lumen intermediary the port and the valve housing. The lumen is relatively flexible and may be fabricated with a radiopaque filler. The method for using the device of this invention permits the measuring of the depth of a stoma by inserting the distal end of a lumen through the opening in the stomach, the lumen having a port near the distal end, the lumen also secured to the first end of an inflatable component member, the port being intermediary the first end and the distal end, the lumen also having indicia thereon, inflating the member and ascertaining the relative distance between the first end in the stomach and the outer layer of skin through the use of the indicia. Additional steps in the method may include keeping the member inflated by use of a valve until the distance is ascertained and deflating the member following ascertaining their distance so as to permit the lumen to be withdrawn through the stoma.

15 Claims, 3 Drawing Sheets

STOMA MEASURING DEVICE

TECHNICAL FIELD

The present invention relates generally to a measuring device, and more particularly, to a measuring device which measures the depth of a stoma. Stoma as used herein means an artificial permanent opening, more specifically an opening in the abdominal wall made during a surgical procedure.

BACKGROUND ART

Most individuals in health care facilities are able to achieve sufficient caloric intake through eating prepared meals. However, a sizable number of such patients are unable to ingest enough solid food to meet their body's needs. Examples of these individuals would include stroke or neurologically impaired patients, who have lost their ability to swallow effectively; critically ill, weak or comatose patients, who may be unable to chew sufficient quantities of food; patients suffering from obstructive lesions, such as cancer of the esophagus, who may be unable to swallow their food; and patients with head and neck trauma, such as fractured jaws and gunshot wounds, who cannot chew solid food. For these patients, caloric supplementation through parenteral, also known as intravenous, feeding is not the method of choice.

In response to this problem, liquid foods have been developed for enteral feeding. Typically, enteral feeding utilizes a nasogastric tube to transport the liquid nutritional products from a container through the patient's nasal cavity and thence into the stomach. However, increasing numbers of patients utilize enteral feeding through gastrostomic feeding ports. The gastrostomic feeding device or gastric portal is placed into a stoma and the device typically features a valve to prevent gastric back flow, a relatively cylindrical component which extends through the stoma, and a tip portion which precludes easy withdrawal of the device or port from the stoma.

While it is possible to place the gastric port by means of a surgical procedure utilizing a general anesthetic, the preferred method for placement of these ports is through a percutaneous endoscopic gastrostomy (PEG) which involves the non-invasive surgical creation of an artificial opening into the stomach through the abdominal wall using only a local anesthetic. In a PEG procedure, an endoscope is passed down the throat until its terminus contacts the interior of the stomach. A needle is then externally inserted through the various tissue layers, until it enters the stomach at a predetermined point. The needle is retracted and a guidewire is then inserted through the stoma. The terminal end of the guidewire is grabbed or seized by the endoscope and retracted up the throat. A tapered catheter, preferably plastic, is then externally inserted with the assistance of the guidewire so as to form, upon removal of the catheter, a channel wide enough to accommodate a gastric port. Commercially available examples of these gastric portals are STOMATE (a trademark of Ross Laboratories Division of Abbott Laboratories), the BUTTON, (a trademark of AMT, Inc.) and GASTRO-PORT, (a trademark of Superior Biosystems, Inc.). These gastrostomic feeding ports come in several lengths to correspond to the variance in distance between the interior of the stomach and the patient's outer layer of skin. For example, obese individuals would require gastric ports with a longer connecting tube than a child.

Those skilled in the art of gastric portal placement know that it is important to choose a gastric portal with approximately the correct length of connecting tube. However, rather than resort to trial and error, the prior art has relied on stoma measuring devices which resemble an "L" or a "J" in shape.

These prior stoma measuring devices have a shaft which is longer than the distance between the interior of the stomach and the outer layer of skin. At the distal end of this shaft is a hook portion approximately perpendicular to the shaft, so as to have the device resemble the letter "L", or semi-circular in shape, such that the device resembles the letter "J".

When using the prior art devices, the hook portion is inserted into the stoma, with the relatively rigid shaft following. Some distention of the tissue layers will occur since the distance between the tip of the hook and the shaft is greater than the initial diameter of the stoma. Once the hook portion of the device is believed to be in the interior of the stomach, the hook portion is caused to come into contact with the stomach lining. At this point in time a measurement is taken which in theory corresponds to the distance between the supposed interior of the stomach and the outer layer of skin. However, the prior art devices suffer from three main deficiencies. First, the insertion of the device and/or its subsequent withdrawal may cause a laceration to form due to the irritation associated with the shapes of these devices. Secondly, to the extent that the hook portion becomes deformed while being inserted, the stoma measurement provided may not be accurate and third, the need to position the tip of the hook securely on the stomach lining for the actual measurement, has the potential to injure the stomach lining, especially if the individual performing the measurement is unsure whether the tip has come into sufficient contact with the stomach lining.

It is thus apparent that the need exists for an improved stoma measuring device which provides accurate readings, while at the same time overcoming the drawbacks associated with existing stoma measuring devices.

DISCLOSURE OF THE INVENTION

There is disclosed a stoma measuring device, said device comprising a valve housing containing valve means, a lumen with a port located near its distal end, said lumen having its proximal end secured to said valve housing, and an inflatable component member, said member located near the distal end of said lumen, said member having a first end secured to said lumen intermediary said port and said valve housing.

There is also disclosed a stoma measuring device, said device comprising a valve housing containing valve means, a relatively flexible lumen with a port located near its distal end, said lumen having a tapered tip at its distal end, said lumen having its proximal end secured to said valve housing, said lumen having indicia thereon, and an inflatable component member, said member having a first end secured to said lumen intermediary said port and said valve housing, said member having a second end secured to said lumen intermediary said port and said distal end of said lumen, said member when inflated extending beyond said distal end of said lumen.

There is also disclosed a method for measuring the depth of a stoma, comprising passing a lumen through said stoma into the stomach, said lumen having a port near said distal end, said lumen secured to the first end of an inflatable component member, said port being intermediary said first end and said distal end, said lumen also having indicia thereon, inflating said member, and ascertaining the relative distance between said first end in the stomach and the outer layer of skin through the use of said indicia.

Additionally there is disclosed a stoma measuring device wherein the lumen may be fabricated so as to have a radiopaque filler and may be secured to the valve housing by a solvent bond. Further, the valve housing of the device may be attachable to a syringe by means of a luer lock.

With respect to the method of utilizing the device, additional steps may include keeping the inflatable component member inflated by use of a valve means until the distance between the first end and the outer layer is ascertained. Another step of the method may be the deflation of the member following ascertainment of the distance, so as to permit the lumen to be withdrawn through the stoma.

The present invention provides a stoma measuring device which ensures an accurate measurement, while at the same time overcoming the drawbacks associated with existing stoma measuring devices.

Other aspects and advantages of the invention will be apparent from the following description, the accompanying drawings and the appended claims.

DETAILED DESCRIPTION OF THE INVENTION

Figure 1:
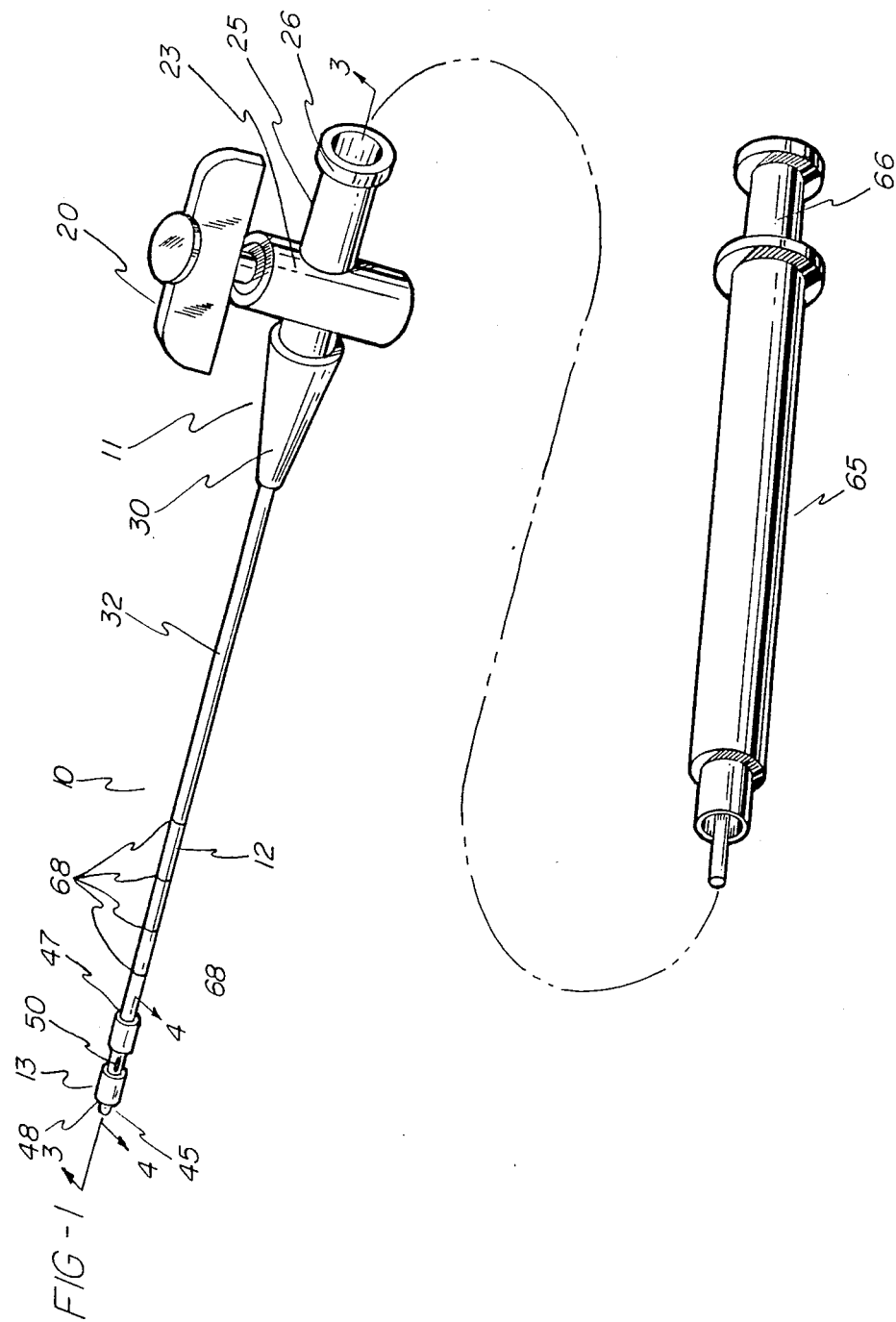
FIG. 1 is a perspective view of the stoma measuring device in accordance with the present invention shown with a syringe which is used in the operation of the invention.

Having a reference to the drawings, attention is directed first to FIG. 1 which illustrates a stoma measuring device embodying this invention designated generally by the numeral 10. The basic components of this device 10 are a valve housing 11, a lumen 12 and a inflatable component member 13.

Figure 2:
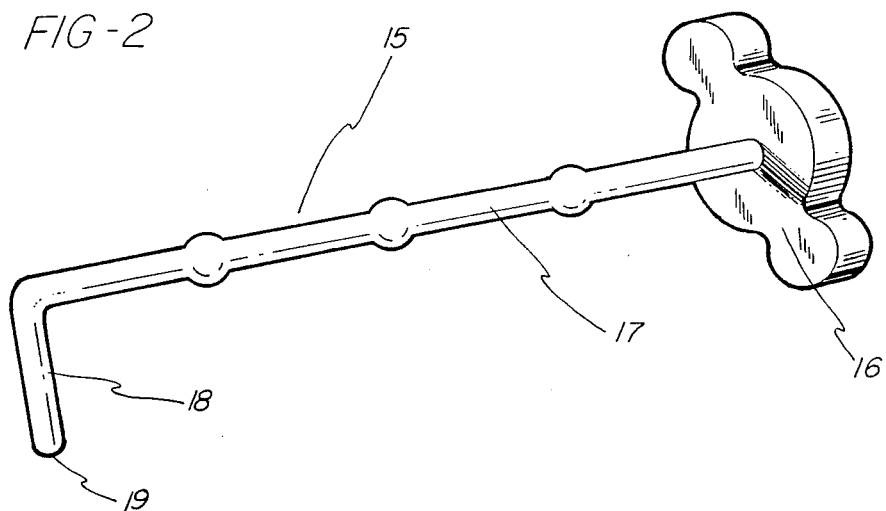
FIG. 2 is a perspective view of a prior art stoma measuring device.

The degree to which the stoma measuring device 10 of this invention departs from the teachings found in the prior are can best be appreciated by a discussion of the prior art device 15 shown in FIG. 2. The prior art devices feature a handle portion 16 connected to a shaft formed from a rigid thermoplastic such as polyethylene. This shaft 17 has a hook portion near its distal end with this hook portion 18 either being normal with respect to the shaft or of a semi-circular configuration such that the shaft and hook either resemble the letter "L" or the letter "J". As can be seen in FIG. 2, the tip 19 of the prior art device 15 is spaced apart from the longitudinal axis of relatively rigid shaft 17.

Figure 3:
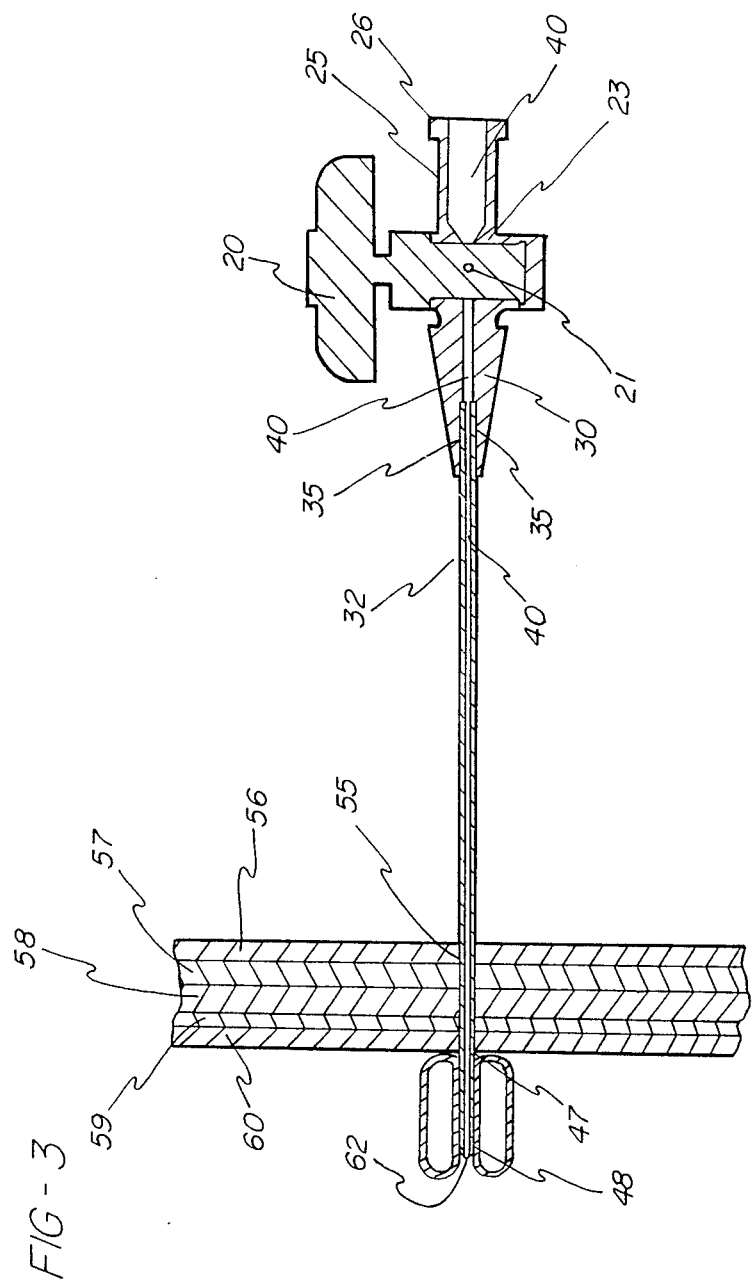
FIG. 3 is a vertical sectional view taken along line 3—3 of FIG. 1 of the device in its operative embodiment.

Comparing FIGS. 1 and 3, valve housing 11 contains valve means 20 with the preferred type of this valve means being a conventional 2-way stopcock valve having an aperture 21 passing therethrough. Stopcock 20 is retained in a stopcock housing 23. Valve housing 11 is preferably formed from a polycarbonate material.

On one side of valve housing 11 preferably is a syringe adaptor 25 having luer locking means 26 at its terminal end. On the opposite side of valve housing 11 from syringe adaptor 25 is a luer slip or lumen adaptor 30 such that lumen 12 may be inserted into the terminal end of the lumen adaptor 30.

Lumen 12 has a proximal end 32 which is secured to the valve housing 11 preferably by means of a solvent bond 35. Thus assembled, an air flow channel 40 extends from the distal end 45 of lumen 12 through lumen adaptor 30 and on through syringe adapter 25. Additionally, when the valve means 20 is in its open position, the air flow channel extends therethrough by means of aperture 21.

Figure 4:
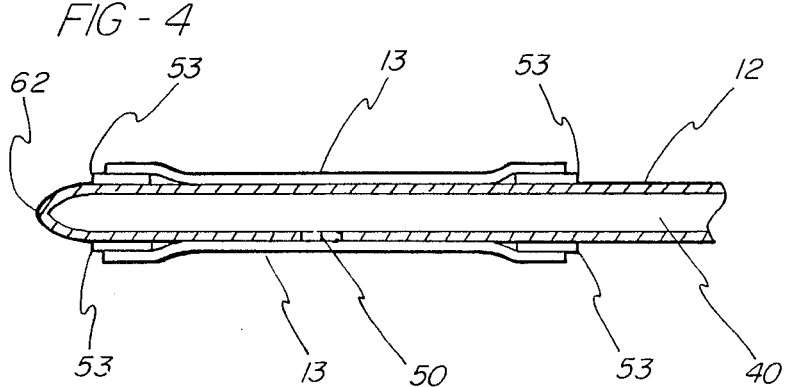
FIG. 4 is a horizontal sectional view on a greatly enlarged scale taken along line 4—4 of FIG. 1 which discloses more clearly the distal end of the lumen of the present invention.

As can be seen in FIGS. 1, 3 and 4, the distal end 45 of lumen 12 has inflatable component member 13 secured thereto. This securing may be by means of adhesive 53 or by solvent bonding of the materials comprising member 13 and lumen 12. Lumen 12 is preferably fabricated from a polyvinyl chloride (PVC), polyurethane, or a silicone elastomer. It should contain no antioxidants or plasticizers, such that it is non-irritative to the tissue through which it must pass, and as such is biocompatible. Furthermore, in the preferred embodiment a radiopaque filler such as barium sulphate may be present to assist in detecting the progress of the insertion of the device through the stoma and thus confirm its placement. Preferably the inflatable component member 13 is fabricated from latex or silicone. In the preferred embodiment, member 13 is secured in two places, at first end 47 and at second end 48. Intermediary the points of attachment of first end 47 and second end 48 to lumen 12 is a port 50 which extends through the side wall of lumen 12.

BEST MODE

In actual operation, the stoma measuring device 10 of this invention is inserted through an artificial opening or stoma 55, created by a surgical or percutaneous endoscopic gastrostomy. In the case where a gastric portal will ultimately be utilized, the lumen 12 and inflatable component member 13 pass through a plurality of tissue layers such as the skin 56, fat 57, muscle layer 58, peritoneum 59, and ultimately through stomach serosa and mucosa 60. To assist in this passage since the stoma may become slightly misaligned, the lumen must be rigid enough and of a sufficient diameter to align the stoma, while at the same time being flexible enough to maneuver if in fact the stoma has become misaligned. Preferably the size of the device is seven french (french is a term used to denote the circumference of a device in millimeters), although sizes ranging from five to fifteen french could be utilized. Furthermore, the durometer of the lumen is preferably 70A, although durometers from 50 to 100A could be selected. Passage of the lumen through the various tissue layers is facilitated by tip 62 having a tapered end, so as to diminish possibility of tissue damage. Once the device 10 is threaded through stoma 55, syringe 65 may be secured to syringe adaptor 25 by the cooperative luer locking means 26. Before completing the securing of the syringe 65 to valve housing 11, sufficient air is allowed to be drawn into syringe 65, with this amount preferably being approximately 3 cc. Upon depression of the syringe plunger 66, air passes through the valve means, which is in its open position such that its aperture is part of air flow channel 40, and thence through lumen 12 and port 50 so as to inflate member 13. Member 13 is elastomeric enough that as it becomes inflated, it extends beyond the distal end 45 of lumen 12. Member 13 is also elastomeric enough to contain a volume of at least 3 cc. Furthermore the diameter of the inflated member is greater than that of the stoma, which is in turn greater than the diameter of lumen 12. When inflated, the distal end 45 of lumen 12 is precluded from being easily withdrawn through the stoma.

Once the member 13 is inflated, valve means 20 may be oriented in a closed position such that the syringe 65 may be detached from syringe adaptor 25, or at the very least, preclude the deflation of member 13. In the inflated mode, the device 10 is used to ascertain the proper length of the feeding tube to be utilized by reliance on indicia 68 on the exterior side walls of lumen 12. Preferably there are a plurality of these indicia, to correspond to the various lengths of feeding tubes available.

The relative distance between first end 47 and the outer layer of skin may then be easily ascertained through the use of the indicia. Once ascertained, the valve means 20 may be returned to an open position, or if the syringe is still attached, it may then be detached, so as to permit the deflation of the inflatable component member 13. Once component member 13 is deflated, the lumen 12 may be withdrawn from the stoma and the gastric port inserted.

INDUSTRIAL APPLICABILITY

The enteral feeding industry has long sought ways to ensure an accurate measurement of the distance between the interior of the stomach lining and the outer surface of the skin while at the same time preventing injury to the stomach lining and irritation of the various tissue layers due to the dimensions associated with the prior art devices. This invention solves this long felt need. While the form of apparatus and method herein described constitute a preferred embodiment of this invention, it is to be understood that the invention is not limited to this precise form of apparatus or method and that changes may be made therein without departing from the scope of the invention which is defined in the appended claims.

What is claimed is:

1. A stoma measuring device comprising.
   regulating means for regulating the passage of air into and out of said device, said regulating means including a valve housing,
   means for passing through a stoma into the stomach, said means for passing including a lumen having a distal end and a proximal end, said proximal end of said lumen secured to said valve housing,
   an inflatable component member, said member located near the optical end of said lumen,
   means for providing the passage of air between said lumen and said inflatable component member, said means for providing the passage of air located near the distal end of said lumen, said inflatable component member having a first end secured to said lumen intermediary said means for providing the passage of air and said valve housing, and a second end secured to said lumen intermediary said means for providing the passage of air and said distal end of lumen, said lumen being totally closed between said second end of the inflatable component member and said distal end, and
   means in combination with said first end of said inflatable component for measuring the depth of the stoma.

2. The device as claimed in claim 1 wherein said lumen as fabricated includes a radiopaque filler.

3. The device as claimed in claim 1 wherein said valve housing includes means for attachment to a syringe.

4. The device as claimed in claim 3 wherein said means for attachment includes a luer lock.

5. The device as claimed in claim 1 wherein said member is fabricated from latex.

6. The device as claimed in claim 1 wherein said regulating means is a stopcock valve.

7. The device as claimed in claim 1 wherein said lumen is secured to said valve housing by a solvent bond.

8. The device as claimed in claim 1 wherein said inflatable member when inflated extends beyond said distal end of lumen and has a diameter adapted to be greater than that of said stoma.

9. The device as claimed in claim 1 wherein said lumen is fabricated from a flexible material.

10. The device as claimed in claim 1 wherein said measuring means includes indicia.

11. The device as claimed in claim 1 wherein said regulating means further includes a stopcock valve.

12. The device as claimed in claim 1 wherein said inflatable member when inflated is adapted to extend beyond said distal end of said lumen and
    wherein said lumen has a diameter adapted to be less than the diameter of the stoma and said inflatable member when inflated has a diameter adapted to be greater than the diameter of the stoma.

13. A method for measuring the depth of a stoma, comprising the steps of
    (1) creating an artificial opening in the body extending through a plurality of tissue layers;
    (2) providing a measuring device which comprises;
    regulating means for regulating the passage of air into and out of said device, said regulating means including a valve housing.
    means for passing through a stoma into the stomach, said means for passing including a lumen having a distal end and a proximal end, said proximal end of said lumen secured to said valve housing,
    an inflatable component member, said member located near the distal end of said lumen,
    means for providing the passage of air between said lumen and said inflatable component member, said means for providing the passage of air located near the distal end of said lumen, said inflatable component member having a first end secured to said lumen intermediary said means for providing the passage of air and said valve housing, and a second secured to said lumen intermediary said means for providing the passage of air and said distal end of said lumen, said lumen being totally closed between said second end the inflatable component member and said distal end, and
    means in combination with said first end of said inflatable component for measuring the depth of the stoma;
    (3) inserting the distal end through said opening;

(4) inflating said inflatable member; and
(5) ascertaining the relative distance between said first end and the outer layer of skin through the use of said means for measuring the depth of the stoma.

14. The method as claimed in claim 13 in which said inflatable member is kept inflated by use of a valve means until said distance is ascertained.

15. The method as claimed in claim 14 in which said inflatable member is deflated and said lumen is withdrawn through said artificial opening.

* * * * *

UNITED STATES PATENT AND TRADEMARK OFFICE
CERTIFICATE OF CORRECTION

PATENT NO. : 4,972,845

DATED : Nov. 27, 1990

INVENTOR(S) : Kent Iversen and Ronald Issac

It is certified that error appears in the above-identified patent and that said Letters Patent is hereby corrected as shown below:

Claim 1, col. 5, line 5 the "." should be a --,-- line 60, "optical end" should be --distal end--.

col. 6, line 2 "of lumen" should be --of said lumen--

Claim 8, col. 6, line 24 "of lumen" should be --of said lumen--

Claim 13, Col. 6, line 46, "." should be --,-- line 60 "second secured" should be --second end secured-- line 63 "end the" should be --end of the--

Signed and Sealed this

Thirtieth Day of June, 1992

*Attest:*

DOUGLAS B. COMER

*Attesting Officer*        *Acting Commissioner of Patents and Trademarks*